United States Patent

Stephen

[11] 4,000,113
[45] Dec. 28, 1976

[54] ACYLATED DERIVATIVES OF 2,6-DIHYDROXY-9-AZABICYCLO[3.3.1]NONANE AND STABILIZED COMPOSITIONS

[75] Inventor: John F. Stephen, New City, N.Y.

[73] Assignee: Ciba-Geigy Corporation, Ardsley, N.Y.

[22] Filed: Sept. 26, 1975

[21] Appl. No.: 617,222

Related U.S. Application Data

[62] Division of Ser. No. 433,421, Jan. 14, 1974, Pat. No. 3,912,742.

[52] U.S. Cl. .............. 260/45.8 N; 260/45.75 N; 260/45.8 NT; 260/45.85 B; 260/45.85 S; 260/45.95 D; 260/45.95 F
[51] Int. Cl.² .................................. C08K 5/34
[58] Field of Search .................. 260/45.8 N

[56] References Cited
UNITED STATES PATENTS

| | | | |
|---|---|---|---|
| 3,190,889 | 6/1965 | Shen | 260/319 |
| 3,435,065 | 3/1969 | Dexter et al. | 260/473 |
| 3,640,928 | 2/1972 | Murayama et al. | 260/23 |
| 3,850,877 | 11/1974 | Cook | 260/45.8 |
| 3,875,169 | 4/1975 | Ramey | 260/293.54 |
| 3,883,477 | 5/1975 | Stephen | 260/45.8 |
| 3,937,711 | 2/1976 | Cook | 260/293.86 |

Primary Examiner—Donald E. Czaja
Assistant Examiner—R. A. White
Attorney, Agent, or Firm—Charles W. Vanecek

[57] ABSTRACT

Compounds having the formula

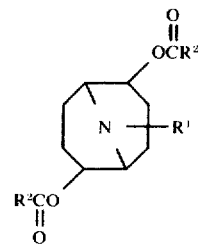

wherein
$R^1$ is hydrogen, alkyl or benzyl and
$R^2$ is alkyl, benzyl or a hindered phenolic group are good light stabilizers and antioxidants. These compounds are prepared by reacting 2,6-dihydroxy-9-azabicyclo[3.3.1]nonane with an appropriate carboxylic acid.

12 Claims, No Drawings

ACYLATED DERIVATIVES OF 2,6-DIHYDROXY-9-AZABICYCLO[3.3.1]NONANE AND STABILIZED COMPOSITIONS

This is a Divisional of application Ser. No. 433,421 filed on Jan. 14, 1974, now U.S. Pat. No. 3,912,742.

DETAILED DISCLOSURE

This invention relates to compounds and organic compositions stabilized therewith. More specifically, these compounds are useful as stabilizers of organic materials which are subject to thermal, oxidative and ultraviolet light degradation. The novel compounds can be represented by the formula

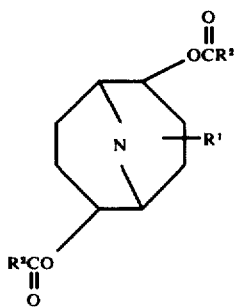

wherein $R^1$ is hydrogen, alkyl having 1 to 12 carbons or benzyl and $R^2$ is alkyl having 1 to 24 carbons, benzyl, alkyl substituted benzyl, or a hindered phenolic group having the formula

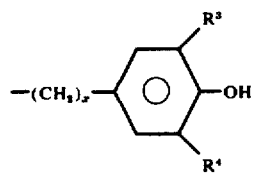

wherein $R^3$ and $R^4$ are lower alkyl having 1 to 8 carbon atoms, and $x$ is an integer of 0 to 2.

The preferred embodiment of the above represented compounds is where $R^1$ is hydrogen, lower alkyl having 1 to 4 carbons and benzyl, and where $R^2$ is alkyl having from 1 to 17 carbons, benzyl or the group

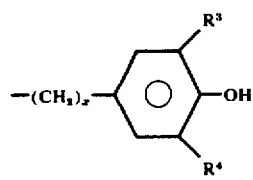

where $x$ is zero, one or 2 and $R^3$ and $R^4$ are branched alkyl such as isopropyl, sec- and tert-butyl, sec- and tert-amyl, sec- and tert-heptyl or sec- and tert-octyl. Most preferably said groups are tert-butyl.

It should be noted that when $R^2$ is alkyl, benzyl, alkyl substituted benzyl or a hindered phenolic group where the integer $x$ is zero, the resulting compounds are good ultraviolet light stabilizers. However, when $R^2$ is a hindered phenolic group where $x$ is one or two, the resulting compounds are particularly good antioxidant and thermal stabilizers.

Esters of 2,6-dihydroxy-9-azabicyclo[3.3.1]nonane can be prepared by reacting 2,6-dihydroxy-9-azabicyclo[3.3.1]nonane with the appropriate carboxylic acid in a suitable solvent, for example, xylene, in the presence of a titanium tetra-alcoholate catalyst such as titanium tetra-isopropylate. 2,6-dihydroxy-9-azabicyclo[3.3.1]nonane can be prepared from 5,10-dioxatricyclo[7.1.0.0$^{4,6}$]decane which can be prepared according to the method described in U.S. Pat. No. 3,241,979.

Esters of 9-substituted-2,6-dihydroxy-9-azabicyclo[3.3.1]nonane can be prepared by reacting the isomeric mixture of diols which results from the reaction of 5,10-dioxatricyclo[7.1.0.0$^{4,6}$]decane with the appropriate primary amine with the appropriate carboxylic acid in a suitable solvent such as xylene in the presence of titanium tetra-alcoholate catalyst such as titanium tetraisopropylate. The mixture of diols above consists of the 9-substituted-2,6-dihydroxy-9-azabicyclo[3.3.1]nonane and the corresponding 9-substituted-2,5-dihydroxy-9-azabicyclo[4.2.1]nonane in about equal amounts. The [4.2.1] ring system in the 9-substituted-2,5-dihydroxy-9-azabicyclo[4.2.1]nonane rearranges to the [3.3.1] system during esterification.

Illustrative examples of the compounds of this invention are:

2,6-diacetoxy-9-azabicyclo[3.3.1]nonane
2,6-diacetoxy-9-butyl-9-azabicyclo[3.3.1]nonane
2,6-distearoyloxy-9-butyl-9-azabicyclo[3.3.1]nonane
2,6-diacetoxy-9-benzyl-9-azabicyclo[3.3.1]nonane
2,6-distearoyloxy-9-benzyl-9-azabicyclo[3.3.1]nonane.

EXAMPLE 1

5,10-Dioxatricyclo[7.1.0.0$^{4,6}$]decane 5,10-Dioxatricyclo[7.1.0.0$^{4,6}$]decane was prepared following the procedure described in U.S. Pat. No. 3,241,979 — a solution of sodium acetate (163.0 g.) in 40% peracetic acid (1315.0 g.) was added dropwise during 2.5 hours to vigorously stirred 1,5-cyclooctadiene (275.3 g.). During the addition the temperature was kept below 25° by use of an ice bath. After the addition was completed the mixture was cooled to 0° and kept at 0° for about 20 hours. The pH of the mixture was adjusted to 11 by the addition of 50% potassium hydroxide solution. The mixture was extracted with 4.5 litres of ether, and the dried (Na$_2$SO$_4$) ether solution was evaporated under reduced pressure to give 294.0 g. of a colorless oil. Distillation through a 3-foot spinning band column gave 200 g. of pure 5,10-dioxatricyclo[7.1.0.0$^{4,6}$]decane, b.p. 56°/0.1 mm. which solidified on standing.

EXAMPLE 2

2,6-Dihydroxy-9-Azabicyclo[3.3.1]nonane 2,6-Dihydroxy-9-azabicyclo[3.3.1]nonane was prepared following the procedure of Stetter and Heckel (Tet. Letters No. 9,801 (1972))

A 1-liter stainless steel stirred autoclave was charged with 5,10-dioxatricyclo[7.1.0.0$^{4,6}$]decane (98.0 g. 0.7 mole) and 400 ml. of ethanol containing 68.0 g. of ammonia. The mixture was stirred and heated at 140° for 5 hours. After cooling and venting the crystalline solid which had separated was collected by filtration. Addition of dioxane to the filtrate produced a second crop of material. The combined crops were recrystallized from methanol to give 31.0 g. of the title compound, m.p. 243°-245°. Concentration of the mother liquor afforded a second crop of 14.0 g. m.p. 235°-238°.

EXAMPLE 3

2,6-Dobutyryloxy-9-Methyl-9-Azabicyclo[3.3.1]nonane

A Fischer and Porter pressure bottle was charged with 5,10-dioxatricyclo[7.1.0.0$^{4,6}$]decane (28.0 gm, 0.2 mole), 50 ml. of ethanol and 40% aqueous methylamine (62.0 g., 0.8 mole). The mixture was heated at 140°-150° for 12 hours. Ethanol, water and excess methylamine were removed under reduced pressure to give an oily residue. Recrystallization from acetone gave 31.1 g. of a 1:1 mixture (as determined by analysis of the NMR spectrum of the mixture) of 2,6-dihydroxy-9-methyl-9-azabicyclo[3.3.1]nonane and 2,5-dihydroxy-9-methyl-9-azabicyclo[3.3.1]nonane m.p. 130°-162°.

To a stirred solution of the diol mixture, 2,6-dihydroxy-9-methyl-9-azabicyclo[3.3.1]nonane and 2,5-dihydroxy-9-methyl-9-azabicyclo[4.2.1]nonane (5.14 g., 0.03 mole) and butyric acid (11.6 g., 0.132 mole) in 150 ml. of dry xylene was added 0.85 ml. of titanium tetraisopropylate. The mixture was heated under reflux for 15 hours water being removed with a Dean-Stark trap. Xylene and excess butyric acid were evaporated under reduced pressure. The oily residue thus obtained was dissolved in ether. Water was added and the mixture was stirred vigorously for about 10 minutes. The precipitated solid was filtered off, the ether layer was separated, washed with 2N sodium hydroxide solution then brine and finally dried oer Na$_2$SO$_4$. Evaporation of the ether gave 8.5 g. of an oil which was distilled under reduced pressure to give 6.4 g. of the above named compound, b.p. 132°-134°/0.02mm.

EXAMPLE 4

2,6-Dibutyryloxy-9-Butyl-9-Azabicyclo[3.3.1]nonane

Under similar conditions, as in Example 3, reaction of 5,10-dioxatricyclo[7.1.0.0$^{4,6}$]decane with n-butylamine led to a mixture of the corresponding isomeric 9-butyl-2,6-dihydroxy-9-azabicyclo[3.3.1]nonane and 9-butyl-2,5-dihydroxy-9-azabicyclo[4.2.1]nonane.

Treatment of this mixture with butyric acid and titanium tetraisopropylate as in Example 3 gave the title compound as an oil.

Analysis Calculated for C$_{20}$H$_{35}$NO$_4$: % Calculated: C, 67.95; H, 9.98; N, 3.96. % Found: C, 67.76; H, 10.05; N, 3.94.

The compounds listed in Table 1 were prepared according to the procedure of Example 3.

Table 1

Acylated Derivatives of 2,6-Dihydroxy-9-Azabicyclo[3.3.1]nonane

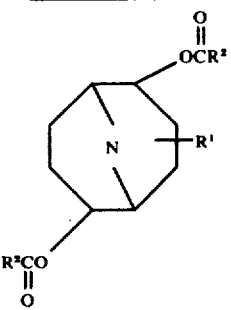

| Example No. | R$^1$= | R$^2$= | |
|---|---|---|---|
| 5 | CH$_3$ | CH$_3$ | b.p. 100–102° C/0.01 mm |
| 6 | CH$_3$ | n-C$_7$H$_{15}$ | oil * |
| 7 | CH$_3$ | n-C$_{17}$H$_{35}$ | m.p. 61–64° C |
| 8 | CH$_3$ | CH$_2$—⟨⟩ | oil * |
| 9 | (CH$_3$)$_2$CH$_3$ | n-C$_7$H$_{15}$ | oil * |
| 10 | CH$_2$—⟨⟩ | n-C$_3$H$_7$ | oil * |
| 11 | CH$_2$—⟨⟩ | n-C$_7$H$_{15}$ | oil * |
| 12 | H | n-C$_7$H$_{15}$ | oil * |
| 13 | H | n-C$_{17}$H$_{35}$ | m.p. 64–66° C |

* Each compound that was an oil was purified by chromatography over silica gel. The microanalytical results for hydrogen, carbon and nitrogen corresponded to the calculated values.

EXAMPLE 14

2,6-bis{3-(3,5-di-tert-butyl-4-hydroxyphenyl)-propionyloxy}-9-methyl-9-azabicyclo[3.3.1]nonane In a nitrogen atmosphere a stirred mixture of the diol mixture 2,6-dihydroxy-9-methyl-9-azabicyclo[3.3.1]nonane and 2,5-dihydroxy-9-methyl-9-azabicyclo[4.2.1]nonane (4.28 g., 0.025 mole), 3-(3,5-di-tert-butyl-4-hydroxyphenyl)propionic acid (15.3 g, 0.055 mole) and 0.7 ml of titanium tetraisopripylate in 100 ml of xylene was heated under reflux in a flask equipped with a Dean-Stark trap for 14 hours. The xylene was evaporated under reduced pressure and the residue thus obtained was dissolved in ether. The ether solution was washed with 5% aqueous sodium hydroxide and then water. The dried (Na$_2$SO$_4$) solution was evaporated under reduced pressure to give an oily residue which was crystallized from petroleum ether. Recrystallization from methanol gave 9.8 g (56.6%) of the title ester, m.p. 107°-109°.

EXAMPLE 15

2,6-bis(3,5-di-tert-butyl-4-hydroxyphenylacetoxy)-9-methyl-9-azabicyclo[3.3.1]nonane Under nitrogen a stirred solution of the diol mixture 2,6-dihydroxy-9-methyl-9-azabicyclo[3.3.1]nonane and 2,5-dihydroxy-9-methyl-9-azabicyclo[4.2.1]nonane (4.28 g, 0.025 mole), 3,5-di-tert-buty 1-4-hydroxyphenylacetic acid (14.55 g, 0.055 mole) and titanium tetraisopropylate (0.7 ml) in 100 ml of xylene was heated under reflux for 18 hours water being removed with a Dean-Stark trap. The xylene was evaporated under reduced pressure and the residue was dissolved in ether. The ether solution was washed with water then 10% aqueous sodium hydroxide and again with water. The dried (Na$_2$SO$_4$) solution was crystallized from petroleum ether and then from hexane to give 4.6 g (28%) of the desired ester, m.p. 98°–100° C.

EXAMPLE 16

In a similar manner, by substituting an equivalent amount of 3,5-di-tert-butyl-4-hydroxybenzoic acid in the above procedure 2,6-bis-(3,5-di-tert-butyl-4-hydroxybenzoyloxy)-9-methyl-9-azabicyclo[3.3.1]nonane is obtained.

The compounds of this invention are stabilizers of organic material normally subject to thermal, oxidative or actinic light deterioration. Materials which are thus stabilized include synthetic organic polymeric substances including homopolymers, copolymers, and mixtures thereof, such as vinyl resins formed from the polymerization of vinyl halides or from the copolymerization of vinyl halides with unsaturated polymerizable compounds, e.g., vinyl esters, α,β-unsaturated acids, α,β-unsaturated esters, α,β-unsaturated ketones, α,β-unsaturated aldehydes and unsaturated hydrocarbons such as butadienes and styrene; poly-α-olefins such as high and low density polyethylene, cross-linked polyethylene, polypropylene, poly(4-methylpentene-1 and the like, including copolymers of α-olefins; such as ethylene-propylene copolymers, and the like; dienes such as polybutadiene, polyisoprene, and the like, including copolymers with other monomers; polyurethanes such as are prepared from polyols and organic polyisocyanates, and polyamides such as polyhexamethylene adipamide and polycaprolactam; polyesters such as polyethylene terephthalates; polycarbonates such as those prepared from bisphenol-A and phosgene; polyacetals such as polyethylene terephthalate polyacetal; polystyrene, polyethyleneoxide; polyacrylics such as polyacrylonitrile; polyphenyleneoxides such as those prepared from 2,6-dimethylphenol and the like; and copolymers such as those of polystyrene containing copolymers of butadiene and styrene and those formed by the copolymerization of acrylonitrile, butadiene and/or styrene.

Other materials which can be stabilized by the compounds of the present invention include lubricating oil of the aliphatic ester type, i.e., di(1,2-ethylene)-azelate, pentaerythritol tetracaproate, and the like; animal and vegetable derived oils, e.g., linseed oil, fat, tallow, lard, peanut oil, cod liver oil, castor oil, palm oil, corn oil, cottonseed oil, and the like; hydrocarbon materials such as gasoline, mineral oil, fuel oil, drying oil, cutting fluids, waxes, resins, and the like, salts of fatty acids such as soaps and the like; and alkylene glycols, e.g., β-methoxyethyleneglycol, methoxytriethyleneglycol, triethylene glycol, octaethyleneglycol, dibutyleneglycol, dipropyleneglycol and the like.

The compounds of this invention are particularly useful as UV light stabilizers and as antioxidants, especially for the protection of polyolefins, for instance, polyethylene, polypropylene, poly(butene-1), poly(pentene-1 ), poly(3-methylbutene-1), poly(4-methylpentene-1), various ethylene-propylene copolymers and the like.

In general, the stabilizers of this invention are employed from about 0.01 to about 5% by weight of the stabilized composition, although this will vary with the particular substrate and application. An advantageous range is from about 0.05 to about 2% and especially 0.1 to about 1%.

For addition to polymeric substrates, the stabilizers can be blended before polymerization or after polymerization, during the usual processing operations, for example, by hot-milling, the composition then being extruded, pressed, blow molded or the lik into films, fibers, filaments, hollow spheres and the like. The heat stabilizing properties of these compounds may advantageously stabilize the polymer against degradation during such processing at the high temperature generally encountered. The stabilizers can also be dissolved in suitable solvents and sprayed on the surface of films, fabrics, filaments or the like to provide effective stabilization. Where the polymer is prepared from a liquid monomer as in the case of styrene, the stabilizer may be dispersed or dissolved in the monomer prior to polymerization or curing.

These compounds can also be used in combination with other additives such as antioxidants, sulfur-containing esters such as distearyl-β-thiodipropionate (DSTDP), dilauryl-β-thiodipropionate (DLTDP) in an amount of from 0.01 to 2% by weight of the organic material, and the like, pourpoint depressants, corrosion and rust inhibitors, dispersing agents, demulsifiers, antifoaming agents, fillers such as glass or other fibers, carbon black, accelerators and the other chemicals used in rubber compounding, plasticizers, color stabilizers, di- and tri-alkyl- and alkylphenyl- phosphites, heat stabilizers, ultraviolet light stabilizers, antiozonants, dyes, pigments, metal chelating agents, dyesites and the like. Often combinations such as these, particularly the sulfur containing esters, the phosphites and/or the ultraviolet light stabilizers will produce superior results in certain applications to those expected by the properties of the individual components.

The following formula represents co-stabilizers which are in certain instances very useful in combination with the stabilizers of this invention:

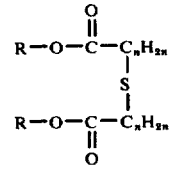

wherein R is an alkyl group having from 6 to 24 carbon atoms; and n is an integer from 1 to 6. Especially useful compounds of this type are dilauryl-β-thiodipropionate and distearyl-β-thiodipropionate. The above co-stabilizers are used in the amount of from 0.01 to 2% by weight of the organic material, and preferably from 0.1 to 1%.

Although the compounds of this invention may to some degree also be effective as thermal stabilizers, if the processing of the polymer is carried out at high temperatures it is advantageous to incorporate additional antioxidants.

In most applications, it is desirable to incorporate into the resin composition, sufficient thermal antioxidants to protect the plastic against thermal and oxidative degradation. The amount of antioxidant required will be comparable to that of the actinic stabilizer. Namely, from about 0.005% to 5% and preferably from 0.01% to 2% by weight Representative of such antioxidants are phosphite esters, such as triphenylphosphite and dibutylphosphite and alkyl arylphosphites such as dibutylphenylphosphite, and the like.

The best results have been obtained with the preferred class of thermal antioxidants, the hindered phenols. These compounds have been found to provide the best thermal stabilization with the least discoloration in the compositions of the invention. Among these phenolic antioxidants are included the following:

di-n-octadecyl(3-5-butyl-4-hydroxy-5-methylbenzyl)-malonate
2,6-di-t-butylphenol
2,2'-methylene-bis(6-t-butyl-4-methylphenol)
2,6-di-t-butylhydroquinone
octadecyl-(3,5-di-t-butyl-4-hydroxybenzylthio)acetate
1,1,3-tris(3-t-butyl-6-methyl-4-hydroxyphenyl)-butane
1,4-bis(3,5-di-t-butyl-4-hydroxybenzyl)-2,3-5,6-tetramethylbenzene
2,4-bis-(3,5-di-t-butyl-4-hydroxyphenoxy)-6-(n-octylthio)-1,3,5-triazine
2,4-bis-(4-hydroxy-3,5-di-t-butylphenoxy)-6-(n-octylthioethylthio)-1,3,5-triazine
2,4-bis-(n-octylthio)-6-(3,5-di-t-butyl-4-hydroxyanilino)-1,3,5-triazine
2,4,6-tris-(4-hydroxy-3,5-di-t-butylphenoxy)-1,3,5-triazine
n-octadecyl-β-(3,5-di-t-butyl-4-hydroxyphenyl)propionate
n-octadecyl-3,5-di-t-butyl-4-hydroxybenzoate
2-(n-octylthio)ethyl-3,5-di-t-butyl-4-hydroxybenzoate
stearamido N,N-bis-{ethylene 3-(3,5-di-t-butyl-4-hydroxyphenyl)propionate}
1,2-propylene glycol bis-{3-(3,5-di-t-butyl-4-hydroxyphenyl)propionate}
pentaerythritol tetrakis-{3-(3,5-di-t-butyl-4-hydroxyphenyl)propionate}
dioctadecyl-3,5-di-t-butyl-4-hydroxybenzylphosphonate
di-n-octadecyl-1-(3,5-di-t-butyl-4-hydroxyphenyl)-ethanephosphonate.

The above phenolic hydrocarbon stabilizers are known and many are commercially available.

The above antioxidants have been listed only for the purpose of illustration and it is important to note that any other antioxidant can be employed with similar improved results. The above exemplified antioxidants and other related antioxidants which are incorporated herein by reference, are disclosed in greater detail in the following patents: Netherlands Patent Specification No. 67/1119, issued Feb. 19, 1968; Netherlands Patent Specification No. 68/03498 issued Sept. 18, 1968; U.S. Pat. Nos. 3,255,191; 3,330,859, 3,644,482, 3,281,505; 3,531,483, 3,285,855; 3,364,250; 3,368,997; 3,357,944 and 3,758,549.

ARTIFICIAL LIGHT EXPOSURE TEST

Deterioration of most polymers caused by ultraviolet light is so slow at ambient temperatures, even in the absence of stabilizers, that testing of the effects of stabilizers generally must be conducted either at higher temperatures or in an accelerated artificial light exposure device in order to yield results in a convenient period of time. The tests conducted on polymers using an artificial light exposure device is described below:

a. Sample Preparation 5 mil Film — Unstabilized polypropylene powder (Hercules Profax 6501) is thoroughly blended with the indicated amounts of additives. The blended material is then milled on a two roll mill for 5 minutes at 182° C.

The milled sheet is then compression molded at 220° C into 5 mil thick film under a pressure of 175 psi and water cooled in the press.

b. Testing Method

This test is conducted in a FS/BL unit, basically of the American Cyanamid design, which consists of 40 tubes of alternating fluorescent sunlamps and black lights (20 of each). The 5 mil sample film which are mounted on 3 inch × 2 inch IR card holders with ¼ inch × 1 inch windows and are placed on a rotating drum 2 inches from the bulbs in the FS/BL unit. The time in hours is noted for the development of 0.5 carbonyl absorbance units as determined on an Infrared Spectrophotometer. The development of carbonyl functional groups in the polymer is proportional to the amount of degradation caused by the ultraviolet light exposure.

The test results reported below were obtaind according to the procedures described above. The amounts of the additives are expressed in weight percent based on the weight of the polymer.

Table II

| Light Stabilization Data in Polypropylene | | | |
|---|---|---|---|
| Example No. | Stabilizer | Time in Hours to 0.5 Carbonyl Absorbance Units | |
| | | Formul A* | Formul B** |
| 17 | Compound of Example 5 | 360 | 800 |
| 18 | Compound of Example 3 | 740 | 990 |
| 19 | Compound of Example 6 | 630 | 1085 |
| 20 | Compound of Example 7 | 410 | 840 |
| 21 | Compound of Example 8 | 295 | 895 |
| 22 | Compound of Example 12 | 390 | 725 |
| 23 | Compound of Example 13 | 380 | 735 |
| 24 | Compound of Example 4 | 810 | 1400 |
| 25 | Compound of Example 9 | 620 | 1440 |
| 26 | Compound of Example 10 | 535 | 1020 |
| 27 | Compound of Example 11 | 460 | 875 |
| 28 | None | 230 | 555 |

Formulation A - The composition contains 0.5% of the indicated stabilizer and 0.2% of di-n-octadecyl (3,5-di-t-butyl-4-hydroxybenzyl)phosphonate which is an antioxidant which prevents oxidative degradation of polypropylene.
**Formulation B - The composition contains 0.25% of the indicated stabilizer, 0.25% of UV absorber 2(2'-hydroxy-3',5'-di-t-butylphenyl)-5-chloro-benzotriazole and 0.2% of antioxidant di-n-octadecyl(3,5-di-tert-butyl-4-hydroxybenzyl) phosphonate.

The compositions of Table II are equally stabilized when {2 2'-hydroxy-3', 5'-di-t-butylphenyl}-5-chlorobenzotriazole is replaced with the following UV absorbers:

a. 2-hydroxy-4-methoxy-5-sulfonbenzophenone trihydrate
b. 2-hydroxy-4-n-octoxybenzophenone
c. {2,2'-thiobis(4-t-octylphenolate)}-n-butylamine nickel II
d. p-octlyphenyl salicylate
e. 2,2'-dihydroxy-4,4'-dimethoxybenzophenone
f. 2{2'-hydroxy-5'-methylphenyl}-benzotriazole Other hindered phenolic antioxidants may be used in place of di-octadecyl(3,5-di-t-butyl-4-hydroxybenzyl)-phosphonate in the above mentioned compositions for example, di-n-octadecyl α-(3-t-butyl-4-hydroxy-4-methylbenzyl)malonate, 2,4-bis (n-octylthio)-6-(3,5- di-t-butyl-4-hydroxyaniline)-1,3,5-triazine, octadecyl 3-(3',5'-di-t-butyl-4'-hydroxyphenyl)propionate, pentaerythritol-tetrakis{3-(3,5-di-t-butyl-hydroxyphenyl)-propionate}, tris-(3,5-di-t-butyl-4-hydroxybenzyl)isocyanurate, respectively.

EXAMPLE 29

Pellets (500 g) of ustabilized nylon-6,6 (Zytel 101, DuPont) are placed in a Kitchen Aid Mixer. With mixing a solution of 0.5% (based on the weight of nylon) of 2,6-distearoyloxy-9-azabicyclo[3.3.1]nonane in 20 ml of methylene chloride is added slowly. Sodium hypophosphite (0.5 gm. 0.1%) is dissolved in 20 ml of water and added slowly with mixing to the nylon pellets after the antioxidant solution has been added and most of the methylene chloride has evaporated. The stabilized pellets are dried at 80° C at <<1 mm Hg. for 4 hours.

The polyamide formulation is extruded at 600° F through at ¼ inch die into a rod which is water cooled and chopped into pellets. A ¾ inch Brabender extruder, equipped with a nylon screw, is used. The pellets are dried at 80° C at <<1 mm for 4 hours.

The dried pellets are reextruded into 5 mil (nominal) monofilament fiber which is subsequently oriented (4:1). The oriented fibers are exposed to outdoor weathering (direct and under glass) and tensile measurement is made periodically. The sample is considered to have failed when it loses 50% of its original tenacity. The sample stabilized with the above noted ester retained tensile strength for a much longer period than the unstabilized sample.

EXAMPLE 30

Unstabilized high impact polystyrene resin is dry blended with 0.01% by weight of the resin of 2,6-dioctanoyloxy-9-azabicyclo[3.3.1]nonane. The resin is then extrusion compounded on a 1 inch 24/1=L/D extruder, melt temperature 500° F and pressed for 7 minutes at a temperature of 163° C and a pressure of 2000 psi into a sheet of uniform thickness of 100 mil. the sheets are then cut into plaques of 2 inch × 2 inch. The plaques are then exposed in a FS/BL exposure device and color measurements made periodically using a Hunter Color Difference Meter Model D25. The polystyrene samples stabilized with the above ester developed the undesirable yellow discoloration substantially later after such discoloration occurred in the unstabilized samples.

EXAMPLE 31

Unstabilized linear polyethylene is solvent blended in methylene chloride with 0.5% by weight of the substrate of 2,6-dioctanoyloxy-9-methyl-9-azabicyclo [3.3.1]-nonane and then vacuum dried. The resin is then extruded at 450° F as described in Example 29. Thereafter, the test procedure of Example 28 is followed and the light stability of the samples determined. Polyethylene stabilized with the above ester is found to be much more stable than the unstabilized polyethylene or the polyethylene stabilized only with an antioxidant.

EXAMPLE 32

A quantity of SBR emulsion containing 100 g of rubber (500 ml of 20% SBR obtained from Texas U.S., Synpol 1500 ) previously stored under nitrogen, is placed in a breaker and stirred vigorously. The pH of the emulsion is adjusted to 10.5 with a 0.5N NaOH solution.

To the emulsion is added 50 ml of 25% NaCl solution. A 6% NaCl solution adjusted with hydrochloric acid to a pH 1.5 is added in a thin stream with vigorous stirring. When pH 6.5 is reached, the rubber begins to coagulate and the addition is slowed down in order to maintain uniform agitation. The addition of the acidic 6% solution is terminated when a pH 3.5 is reached. The coagulated crumb-rubber slurry at pH 3.5 is stirred for ½ hour.

The coagulated rubber is isolated by filtration through cheese cloth, and rinsed with distilled water. After three subsequent washings with fresh distilled water, the coagulated rubber is dried, first at 25 mm Hg and finally to constant weight under high vacuum (<1mm) at 40°–45° C.

The dried rubber (25 g) is heated under nitrogen at 125° C in a Brabender mixer and to this is added with mixing 0.5% of 2,6-dibutyryloxy-9-methyl-9-azabicyclo[3.3.1]nonane. The composition is mixed for 5 minutes after which it is cooled and compression molded at 125° C into 5 inch × 0.025 inch plaques.

The plaques are exposed to a xenon arc weatherometer and the color measurement (L-b) is made after 45, 125 and 290 hours. The samples stabilized with the above ester is found to be much more light stable than the unstabilized samples.

EXAMPLE 33

To 50 g of polyacetal resin containing 0.1% of an acid scavenger, dicyandiamide, is added 0.2% by weight of 2,6-butyryloxy-9-butyl-9-azabicyclo [3.3.1]-nonane, and milled for 7 minutes at 200° C in a Brabender Plastirecorder. The milled formulation is subsequently pressed into a 40 mil sheet at 215° C at 350 psi for 90 seconds then cooled quickly in a cold press at 350 psi. The stabilized sheets are then remolded for 2 minutes at contact pressure and for 3 minutes at 300 psi at 215° C to give plaques 1½ inch × 2¼ inch × 125 mil. Thereafter, the testing procedure of Example 28 is followed to determine the light stability of the samples. The stabilized samples are found to be much more stable than the unstabilized samples.

EXAMPLE 34

Unstabilized thoroughly dried polyethylene terephthalate chips are dry blended with 1.0% of 2,6-dioctanoyloxy-9-butyl-9-azabicyclo[3.3.1]nonane. 60/10 denier multifilament is melt spun at a melt temperature of 290° C. The oriented fiber is wound on white cards and exposed in a Xenon Arc Fadeometer. Color measurements are made periodically with a Hunter Color Difference Meter Model D25. The stabilized samples are found to be much more light stable than the unstabilized samples.

EXAMPLE 35

Unstabilized polypropylene powder (Hercules Profax 6501) was thoroughly blended with the stabilizers indicated in Table III below. The blended materials were then milled on a two-roll mill at 182° C for 10 minutes, after which time the stabilized polypropylene was sheeted from the mill and allowed to cool.

The milled polypropylene sheets were then cut into pieces and pressed for 7 minutes on a hydraulic press at 218° C, 2,000 pounds per square inch pressure. The resulting plaques of 25 mil thickness were tested for resistance to accelerated aging in a forced draft oven at 150° C. When the plaques showed the first signs of decomposition (e.g., cracking or brown edges) they were considered to have failed. The results were as follows:

TABLE III

Oven Aging of Polypropylene

| Stabilizer | Time to Failure in Hours Formulations | | |
|---|---|---|---|
| | A[1] | B[2] | C[3] |
| Compound of Ex. 14 | 860 | 850 | 870 |
| Compound of Ex. 15 | 670 | 680 | 635 |
| No stabilizer | 3 | | |

[1]Formulation A contains 0.2% of the indicated stabilizer of this invention.
[2]Formulation B contains 0.2% of the indicated stabilizer and 0.5% of UV absorber 2(2'-hydroxy-3',5'-di-tert-butylphenyl)-5-chlorobenzotriazole.
[3]Formulation C contains 0.1% of the indicated stabilizer and 0.3% of dilaurylthiodipropionate.

What is claimed is:

1. A composition of matter comprising a synthetic organic polymer subject to deterioration and from about 0.01 to about 5% by weight of the composition of a stabilizing compound of the formula

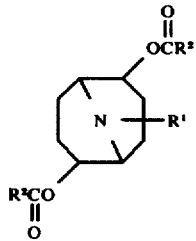

wherein
  $R^1$ is hydrogen, alkyl having 1 to 12 carbons and benzyl, and
  $R^2$ is alkyl having 1 to 24 carbons, benzyl, alkyl substituted benzyl or a hindered phenolic group having the formula

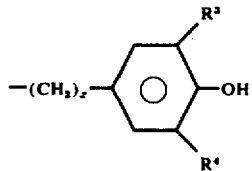

wherein
  $R^3$ and $R^4$ are lower alkyl having 1 to 8 carbons and
  $x$ is an integer of 0 to 2.

2. A composition of claim 1 which contains additionally a stabilizing amount of a UV absorber selected from the group consisting of hydroxy benzophenones, hydroxyphenyl benzotriazoles, aromatic esters of salicylic acid and nickel amine complexes of thiobis-phenols.

3. A composition of claim 1 which contains additionally 0.01 to 2% of a thiosynergist having the formula

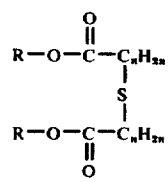

wherein R is an alkyl group having from 6 to 24 carbon atoms and $n$ is an integer from 1 to 6.

4. A composition of claim 1 which contains additionally 0.005 to 5% of a phenolic antioxidant.

5. A composition of claim 1 which contains additionally
  a. 0.005 to 5% of a phenolic antioxidant and
  b. a stabilizing amount of a UV absorber selected from the group consisting of hydroxy benzophenones, hydroxyphenyl benzotriazoles, aromatic esters of salicylic acid and nickel amine complexes of thiobis-phenols.

6. A composition of claim 1 wherein the synthetic organic polymer is a polyolefin.

7. A composition of claim 6 wherein the polyolefin is polypropylene.

8. A composition of claim 1 wherein
  a. the synthetic organic polymer is a polyolefin and
  b. the stabilizing compound of formula I is selected from 2,6-bis{3-(3,5-di-tert-butyl-4-hydroxyphenyl)-propionyloxy}-9-methyl-9-azabicyclo[3.3.1]nonane and 2,6-bis(3,5-di-tert-butyl-4-hydroxyphenylacetoxy)-9-methyl-9-azabicyclo[3.3.1]nonane.

9. A composition of claim 2 wherein
  a. the synthetic organic polymer is a polyolefin,
  b. the stabilizing compound of formula I is selected from 2,6-bis{3-(3,5-di-tert-butyl-4-hydroxyphenyl)-propionyloxy}-9-methyl-9-azabicyclo[3.3.1]nonane and 2,6-bis(3,5-di-tert-butyl-4-hydroxyphenylacetoxy)-9-methyl-9-azabicyclo[3.3.1]nonane and
  c. the UV absorber is selected from 2(2'-hydroxy-3',5'-di-tert-butylphenyl)-5-chlorobenzotriazole, 2(2'-hydroxy-5'-methylphenyl)-benzotriazole, and 2-hydroxy-4-n-octoxybenzophenone.

10. A composition of claim 3 wherein
  a. a synthetic organic polymer is a polyolefin,
  b. the stabilizing compound of formula I is selected from 2,6-bis {3-(3,5-di-tert-butyl-4-hydroxyphenyl)propionyloxy}-9-methyl-9-azabicyclo[3.3.1]nonane and 2,6-bis(3,5-di-tert-butyl-4-hydroxyphenylacetoxy)-9-methyl-9-azabicyclo[3.3.1]nonane and
  c. the thiosynergist is selected from dilauryl-β-thiodipropionate and distearyl-β-thiodipropionate.

11. A composition of claim 4 wherein
  a. the synthetic organic polymer is a polyolefin,
  b. the stabilizing compound of formula I is selected from 2,6-dibutyryloxy-9-methyl-9-azabicyclo[3.3.1]nonane, 2,6-di-n-octanoyloxy-9-methyl-9-azabicyclo[3.3.1]nonane, 2,6-dibutyryloxy-9-butyl-9-azabicyclo-[3.3.1]nonane, 2,6-di-n-octanoyloxy-9-butyl-9-azabicyclo[3.3.1]nonane, and 2,6-dibutyryloxy-9-benzyl-9-azabicyclo[3.3.1]nonane, and
  c. the phenolic antioxidant is selected from n-octadecyl-β-(3,5-di-t-butyl-4-hydroxyphenyl)propionate, di-n-octadecyl(3,5-di-t-butyl-4-hydroxybenzyl)-phosphonate, pentaerythritol-tetrakis[3-(3,5-di-t-butyl-4-hydroxyphenyl)propionate], and tris-(3,5-di-t-butyl-4-hydroxybenzyl)isocyanurate.

12. A composition of claim 5 wherein
a. the synthetic organic polymer is a polyolefin,
b. the stabilizing compound of formula 1 is selected from 2,6-dibutyryloxy-9-methyl-9-azabicyclo[3.3.1]nonane, 2,6-di-n-octanoyloxy-9-methyl-9-azabicyclo[3.3.1]nonane, 2,6-dibutyryloxy-9-butyl-9-azabicyclo[3.3.1]nonane, 2,6-di-n-octanoyloxy-9-butyl-9-azabicyclo[3.3.1]nonane, and 2,6-dibutyryloxy-9-benzyl-9-azabicyclo[3.3.1]nonane, and
c. the phenolic antioxidant is selected from n-octadecyl 3-(3,5-di-t-butyl-4-hydroxyphenyl)propionate, di-n-octadecyl(3,5-di-t-butyl-4-hydroxybenzyl)-phosphonate, pentaerythritol-tetrakis[3-(3,5-di-t-butyl-4-hydroxyphenyl)propionate], and tris-(3,5-di-t-butyl-4-hydroxybenzyl)isocyanurate, and
d. the UV absorber is selected from 2(2'-hydroxy-3',5'-di-tert-butylphenyl)-5-chlorobenzotriazole, 2(2'hydroxy-5'-methylphenyl)-benzotriazole, and 2-hydroxy-4-n-octoxybenzophenone.

* * * * *